(12) United States Patent
Swoyer et al.

(10) Patent No.: US 6,754,536 B2
(45) Date of Patent: Jun. 22, 2004

(54) IMPLANTABLE MEDICAL DEVICE AFFIXED INTERNALLY WITHIN THE GASTROINTESTINAL TRACT

(75) Inventors: John M. Swoyer, Andover, MN (US); Warren Starkebaum, Plymouth, MN (US)

(73) Assignee: Medtronic, Inc, Mpls, MN (US)

( * ) Notice: Subject to any disclaimer, the term of this patent is extended or adjusted under 35 U.S.C. 154(b) by 325 days.

(21) Appl. No.: 10/059,533

(22) Filed: Jan. 30, 2002

(65) Prior Publication Data

US 2002/0103424 A1 Aug. 1, 2002

Related U.S. Application Data

(60) Provisional application No. 60/265,513, filed on Jan. 31, 2001.

(51) Int. Cl.[7] .................................................. A61N 1/36
(52) U.S. Cl. ......................................................... 607/40
(58) Field of Search ............................................ 607/40

(56) References Cited

U.S. PATENT DOCUMENTS

| | | | |
|---|---|---|---|
| 3,411,507 A | 11/1968 | Wingrove | 607/40 |
| 3,835,864 A | 9/1974 | Rasor et al. | 607/36 |
| 5,188,104 A | 2/1993 | Wernicke et al. | 607/40 |
| 5,263,480 A | 11/1993 | Wernicke et al. | 607/118 |
| 5,292,394 A | 3/1994 | Cord et al. | 204/298.39 |
| 5,423,872 A | 6/1995 | Cigaina | 607/40 |
| 5,425,751 A | 6/1995 | Baeten et al. | 607/28 |
| 5,507,289 A | 4/1996 | Essen-Moller | 600/348 |
| 5,540,730 A | 7/1996 | Terry, Jr. et al. | 607/40 |
| 5,690,691 A | 11/1997 | Chen et al. | 607/40 |

(List continued on next page.)

FOREIGN PATENT DOCUMENTS

| | | | | |
|---|---|---|---|---|
| WO | WO 92/13592 A1 | 8/1992 | | A61N/1/05 |
| WO | WO 02/04068 A1 | 1/2002 | | A61N/1/36 |

OTHER PUBLICATIONS

P. Biancani et al., "Mechanical Characteristics of the Cat Pylorus", *Gastroenterology*, 1980, vol. 78, pp. 301–309.

M. Costa et al., "Sensory Nerves of the Intestines: Role in Control of Pyloric Region of Dogs", *Sensory Nerves And Neuropeptides In Gastroenterology*, 1991, pp. 199–211, Plenum Press, New York.

R. Edin, "The Vagal Control of the Pyloric Motor Function", *ACTA Physiologica Scandinavica Supplementum 485*, Goteborg 1980, pp. 1–30.

(List continued on next page.)

*Primary Examiner*—Carl Layno
(74) *Attorney, Agent, or Firm*—Thomas F. Woods; Keith M. Campbell; Thomas G. Barry

(57) ABSTRACT

A GI tract stimulator and/or monitor IMD comprising a housing enclosing electrical stimulation and/or monitoring circuitry and a power source and an elongated flexible member extending from the housing to an active fixation mechanism adapted to be fixed into the GI tract wall is disclosed. After fixation is effected, the elongated flexible member bends into a preformed shape that presses the housing against the mucosa so that forces that would tend to dislodge the fixation mechanism are minimized. The IMD is fitted into an esophageal catheter lumen with the fixation mechanism aimed toward the catheter distal end opening whereby the bend in the flexible member is straightened. The catheter body is inserted through the esophagus into the GI tract cavity to direct the catheter distal end to the site of implantation and fix the fixation mechanism to the GI tract wall. The IMD is ejected from the lumen, and the flexible member assumes its bent configuration and lodges the hermetically sealed housing against the mucosa. A first stimulation/sense electrode is preferably an exposed conductive portion of the housing that is aligned with the bend of the flexible member so that it is pressed against the mucosa. A second stimulation/sense electrode is located at the fixation site.

30 Claims, 6 Drawing Sheets

U.S. PATENT DOCUMENTS

| | | | | |
|---|---|---|---|---|
| 5,716,392 | A | 2/1998 | Bourgeois et al. | 607/32 |
| 5,861,014 | A | 1/1999 | Familoni | 607/40 |
| 6,026,326 | A | 2/2000 | Bardy | 607/40 |
| 6,083,249 | A | 7/2000 | Familoni | 607/40 |
| 6,104,965 | A | 8/2000 | Lim et al. | 700/112 |
| 6,216,039 | B1 | 4/2001 | Bourgeois | 607/40 |
| 6,243,607 | B1 | 6/2001 | Mintchev et al. | 607/40 |
| 6,258,896 | B1 | 7/2001 | Abuelyaman et al. | 525/437 |
| 6,453,199 | B1 * | 9/2002 | Kobozev | 607/40 |
| 6,535,764 | B2 * | 3/2003 | Imran et al. | 607/40 |
| 6,542,776 | B1 * | 4/2003 | Gordon et al. | 607/40 |

OTHER PUBLICATIONS

R. Edin et al., "Evidence for Vagal Enkephalinergic Neural Control of the Feline Pylorus and Stomach", *Gastroenterology*, 1980, vol. 78, pp. 492–497.

W. Hasler, "The Physiology of Gastric Motility and Gastric Emptying", *Textbook of Gastroenterology*, 1995, $2^{nd}$ Ed., vol. 1, pp. 188–192, J.B. Lippincott Company, Philadelphia.

T. Hausken et al., "Antroduodenal Motility Studied by Real–Time Ultrasonography", *Gastroenterology*, 1991, vol. 100, pp. 59–63.

L.A. Houghton et al., "Relationship of the Motor Activity of the Antrum, Pylorus, and Duodenum to Gastric Emptying of a Solid–Liquid Mixed Meal", *Gastroenterology*, 1988, vol. 94, No. 6, pp. 1285–1291.

K.A. Kelly et al., "Duodenal–Gastric Reflux And Slowed Gastric Emptying By Electrical Pacing of the Canine Duodenal Pacesetter Potential", *Gastroenterology*, 1977, vol. 72, No. 9, pp. 429–433.

K.A. Kelly, "Gastric Emptying of Liquids and Solids: Roles of Proximal and Distal Stomach", *American Journal Physiological*, Aug. 1980, vol. 2, pp. G71–G76.

S.H. Lerman et al., "Pyloric Motor Response to Sympathetic Nerve Stimulation in Dogs", *Surgery*, Apr. 1981, vol. 89, No. 4, pp. 460–465.

Y. Lopez et al., "Central and Peripheral Control of Post-prandial Pyloric Motility by Endogenous Opiates and Cholecystokinin in Dogs", *Gastroenterology*, 1991, vol. 101, No. 5, pp. 1249–1255.

C.H. Malbert et al., "Vagal Control of Pyloric Resistance", *Am. J. Physiol.*, Oct. 1995, vol. 269 (*Gastointest. Liver Physiol.* vol. 32) pp. G558–G569.

C.T. Mroz et al., "The Role of the Extrinsic Antral Nerves in the Regulation of Gastric Emptying", *Surgery, Gynecology& Obstetrics*, Sep. 1977, vol. 145, pp. 369–377.

S.K. Sarna et al., "Gastric Pacemakers", *Gastroenterology*, 1976, vol. 70, No. 2, pp. 226–231.

K. Schulze–Delrieu et al., "Neuromuscular Differentation of the Human Pylorus",*Gastroenterology*, 1983, vol. 84, No. 2, pp. 287–292.

Swain et al., "An Endoscopically Deliverable Tissue–Transfixing Device for Securing Biosensors in the Gastrointestinal Tract," *Gastrointestinal Endoscopy*, 1994, vol. 40, No. 6, pp. 730–734.

M. Yoshioka et al. "Effect of 5–Hydroxytryptamine on Gastric Motility and Efferent Gastric Vagus Nerve Activity in Rats", *Research Communications in Chemical Pathology and Pharmacology*, Oct. 1990, vol. 70, No. 1, pp. 3–10.

Enterra™ Therapy 4301—Technical Manual, Medtronic, Inc., 2000, pp. 1–34.

Enterra™ Therapy 4351—Technical Manual, Medtronic, Inc., 2001, pp. 1–33.

Model 4300 Permanent, Unipolar, Intramuscular Lead—Technical Manual, Medtronic, Inc., Jul. 1994, pp. 1–18.

Itrel® 3 System—Physician and Hospital Staff Manual, Model 7425 Implantable Pulse Generator (IPG), Medtronic, Inc., 2001, pp. 1–60.

* cited by examiner

IMPLANTABLE MEDICAL DEVICE AFFIXED INTERNALLY WITHIN THE GASTROINTESTINAL TRACT

RELATED APPLICATIONS

This application claims priority to provisional U.S. Application Ser. No. 60/265,513, filed Jan. 31, 2001.

FIELD OF THE INVENTION

The present invention pertains to implantable medical devices (IMDs), particularly gastrointestinal stimulator and/or monitor IMDs adapted to be implanted within the interior of the gastrointestinal tract having one or more than one stimulation/sense electrode attached to or pressing against an interior surface site of the gastrointestinal tract wall to conduct electrical stimulation to the site and to conduct electrical signals of the GI tract from the site or other physiologic signals from the interior of the gastrointestinal tract.

BACKGROUND OF THE INVENTION

The GI tract comprises the esophagus, the stomach, the small intestine, the large intestine, the colon, and the anal sphincter and is generally described as having a tract axis. Like other organs of the body, most notably the heart, these organs naturally undergo regular rhythmic contractions. In particular these contractions take the form of peristaltic contractions and are essential for the movement of food through each of the respective organs. Like the heart, these contractions are the result of regular rhythmic electrical depolarizations of the underlying tissue.

In some individuals, however, either the regular rhythmic peristaltic contractions do not occur or the regular rhythmic electrical depolarizations do not occur or both do not occur. In each of these situations the movement of food may be seriously inhibited or even disabled. Such a condition is often called "gastroparesis" when it occurs in the stomach. Gastroparesis is a chronic gastric motility disorder in which there is delayed gastric emptying of solids or liquids or both. Symptoms of gastroparesis may range from early satiety and nausea in mild cases to chronic vomiting, dehydration, and nutritional compromise in severe cases. Similar motility disorders occur in the other organs of the GI tract, although by different names.

Diagnosis of gastroparesis is based on-demonstration of delayed gastric emptying of a radio-labeled solid meal in the absence of mechanical obstruction. Gastroparesis may occur for a number of reasons. Management of gastroparesis involves four areas: (1) prokinetic drugs, (2) antiemetic drugs, (3) nutritional support, and (4) surgical therapy (in a very small subset of patients.) Gastroparesis is often a chronic, relapsing condition; 80% of patients require maintenance antiemetic and prokinetic therapy and 20% require long-term nutritional supplementation. Other maladies such as tachygastria or bradygastria can also hinder coordinated muscular motor activity of the GI tract, possibly resulting in either stasis or nausea or vomiting or a combination thereof.

The undesired effect of these conditions is a reduced ability or complete failure to efficiently propel intestinal contents down the digestive tract. This results in malassimilation of liquid or food by the absorbing mucosa of the intestinal tract. If this condition is not corrected, malnutrition or even starvation may occur. Moreover nausea or vomiting or both may also occur. Whereas some of these disease states can be corrected by medication or by simple surgery, in most cases treatment with drugs is not adequately effective, and surgery often has intolerable physiologic effects on the body.

The concept of electrically stimulating the gastrointestinal tract to restore its proper function originated many years ago, and one early approach is disclosed in commonly assigned U.S. Pat. No. 3,411,507. The '507 patent discloses a system for gastrointestinal stimulation which uses an electrode positioned on a nasogastric catheter and an electrode secured to the skin over the abdomen. In operation, the nasogastric catheter is inserted into the patient's stomach while the patient is lying down such that the electrode is positioned in close proximity to the pylorus of the stomach. Electrical stimulation is delivered for the first five seconds of every minute until peristaltic activity is initiated. The '507 patent also discloses using electrical stimulation of the same order of magnitude as the normal range of periodicity of the inherent peristaltic pacemaker action of the duodenum. The stimulation process is discontinued after the first bowel movement. The '507 patent system is a short-term device that is only useful for patients in a hospital setting, and particularly non-ambulatory patients.

Sensing of the peristaltic electrical wave and gastrointestinal stimulation at various sites on or in the GI tract wall of the digestive system or nerves associated therewith have been conducted to diagnose and treat these various conditions over the years since the publication of the '507 patent. Fully implantable gastrointestinal stimulation systems have been developed and clinically implanted in patient's bodies allowing the patients to be ambulatory. The history and breadth of such sensing and GI tract stimulation is set forth in commonly assigned U.S. Pat. Nos. 5,507,289, 6,026,326, 6,104,965, 6,216,039, and in further U.S. Pat. Nos. 5,690, 691 and 6,243,607, for example. The implantable gastrointestinal stimulation systems are referred to as "pacemakers" in certain of these patents and the literature because of their resemblance to implantable cardiac pacemakers in structure and function.

In such fully implantable gastrointestinal stimulation systems, electrical stimuli are applied from an implantable pulse generator (IPG) through elongated leads and lead borne electrodes affixed at sites in the body of the patient or the GI tract wall or the vagus nerve that permit the electrical stimulus to produce a local contraction of a desired portion of the GI tract. The IPG is typically implanted below the skin surface in the abdominal region and leads coupled to the IPG extend to sites of the gastrointestinal tract and/or the vagus nerve where stimulation/sense electrodes are affixed.

The sites of the GI tract wall typically comprise the outermost serosa or sub-serosally in the inner, circumferential and longitudinal (and oblique in the case of the stomach) smooth muscle layers referred to as the "muscularis externa" (although the above referenced '691 patent suggests locating the electrodes within the stomach cavity against the inner stomach surface mucosa). The above-referenced '607 patent discloses one method and system for electrical stimulation of smooth muscle with intact local gastric nerves comprising a portion of the GI tract. The electrical stimulation of the smooth muscle effects local contractions at sites of a portion of the GI tract that are artificially propagated distally therethrough in order to facilitate or aid at least a partial emptying of such portion. This stimulation attempts to create a simulated system that reproduces the spatial and temporal organization of normal gastric electrical activity by creating and controlling local circumferential non-propagated contractions. In this simulated gastric pacing system, each local circumferential contraction is invoked by applying an electrical stimulus to the smooth muscle circumferentially about the portion of the GI tract in a plane substantially perpendicular to the longitudinal axis of the portion. The electrical stimulus is applied at a proximal location and at least one distal location. The distal location is in axially spaced relationship relative to the proximal location. Further, the applied electrical stimulus is selected to be sufficient to stimulate the smooth muscle to produce the local circumferential contractions at the proximal and distal locations.

The Medtronic® Itrel III® Model 7425 IPG and pairs of the unipolar Model 4300 or Model 4301 or Model 4351 "single pass" leads available from MEDTRONIC, INC. have been implanted to provide stimulation to sites in the stomach wall to treat chronic nausea and vomiting associated with gastroparesis. The unipolar electrode of these leads comprises a length of exposed lead conductor and is of the type disclosed in commonly assigned U.S. Pat. Nos. 5,425,751, 5,716,392 and 5,861,014. The above-referenced '039 patent and the '014 patent disclose the Model 4300 lead sewn through the serosa laterally into the muscularis externa to dispose the stimulation/sense electrode therein. A large incision is necessary to access the site, and a needle is used to perforate the serosa and muscularis externa laterally without fully penetrating the wall and to draw the stimulation/sense electrode into the muscularis externa. A laparascopic approach can be taken, but it is difficult to maneuver the needle to effect the fixation of the stimulation/sense electrode at the site. It is suggested in the '039 patent that two or more electrodes of this type can be formed along the length of the lead body that would be sewn laterally through and disposed within the muscularis externa.

A further U.S. Pat. No. 5,292,394 discloses a percutaneous system that provides for temporary stimulation, sensing, delivery of fluids and nutrients, and pH sensing within the gastrointestinal tract. A plurality of distal stimulation/sense electrodes are located within the stomach cavity pressing against the mucosa, and distal pressure and pH sensors are located in the stomach cavity and the small intestine. The sensors and stimulation/sense electrodes are electrically coupled to an external pulse generator/controller by lead conductors extending through a percutaneously introduced access device or tube that the distal components were introduced through. Fluids can also be introduced directly into the stomach or withdrawn from the stomach. The percutaneous pathway is problematic in that the seal around the percutaneous access device that is necessary to prevent leakage of stomach acid into the peritoneal cavity or just subcutaneously around the device.

Ways of attaching pH sensors within the esophagus via the patient's mouth employing an endoscope are disclosed in U.S. Pat. No. 6,258,896. The attachment embodiments disclosed in the '896 patent include use of a loop drawn about a mass of mucosal tissue, a tether tied to a tooth in the patient's mouth, and a recital of the use of hooks, barbs, sutures, tacks, staples, other structures that penetrate the mucosa. It is also suggested that the fixation mechanism be made biodegradable so that the biosensor capsule would be released after a monitoring time period and pass through the GI tract.

Ways of attaching pH sensors within the stomach via the mouth employing an endoscope are disclosed in an article by Swain et al. entitled "An endoscopically deliverable tissue-transfixing device for securing biosensors in the gastrointestinal tract", *GASTROINTESTINAL ENDOSCOPY* vol. 40, no. 6, pp. 730–734, 1994. The attachment mechanism involves use of suction to draw a fold of the stomach wall together and insertion of a preformed, Nylon, H-shaped tag through the fold of the stomach wall. While pH sensors are described, it is suggested that the same equipment and fixation mechanism can be employed to fix other medical devices within the stomach, including "electrical pacemakers", presumably to stimulate the stomach wall. No specific sensing or stimulation electrodes are described.

In the field of cardiac stimulation, cardiac pacing leads having bipolar and unipolar pace/sense electrodes have long been used in conjunction with pacing system IPGs to conduct pacing pulses generated by the IPG to a site of the heart and cardiac signals from the site to the IPG. Pacing leads are typically provided with a passive fixation or an active fixation mechanism at the lead body distal end that is passively or actively engaged with cardiac tissue to anchor a distal tip electrode at a desired site in or on the heart. Passive fixation generally involves an atraumatic fixation lodging the distal electrode against the endocardium or within a coronary blood vessel. Positive or active fixation generally involves a more traumatic penetration of a fixation mechanism into the myocardium from an endocardial or epicardial surface, and the active fixation mechanism commonly comprises a distal pace/sense electrode. Typically, the active fixation mechanism comprises the single pace/sense electrode or one of the bipolar pace/sense electrodes, but can be separate and electrically isolated from the pace/sense electrodes.

Endocardial pacing leads having either active fixation or passive fixation mechanisms are implanted by a transvenous route into a heart chamber to locate the distal pace/sense electrode(s) at a selected site in the heart chamber where an active or passive fixation mechanism is deployed to maintain the pace/sense electrode affixed at the site. Endocardial active fixation pacing leads typically employ extendable and retractable helixes of hooks that are retracted during introduction and are extended distally from the lead body distal end at the site of attachment.

Epicardial pacing leads are implanted by exposure of the epicardium of the heart through a limited thoracotomy. The distal end of the epicardial lead formed with one or two pace/sense electrodes and an active fixation mechanism supported by an electrode head is affixed through the epicardium and within the myocardium. Active fixation mechanisms of epicardial pacing leads typically comprise a tissue penetrating, self-affixing mechanism extending away from a support or base or plate of the electrode head. The fixation mechanism is forced into the myocardium typically employing an insertion tool engaging the electrode head until it is fully seated within the myocardium and the plate bears against the epicardium. The plate is typically formed with a tissue ingrowth encouraging fabric or lattice, whereby tissue ingrowth about the plate assists in chronic anchoring to the heart.

The dislodgement of pace/sense electrodes and the fracture of the lead conductor or the insulation about it were serious concerns in the early years of implantable cardiac pacemakers. A combined pacemaker IPG, pace/sense electrodes, and active fixation barb mechanism are disclosed in U.S. Pat. No. 3,835,864 that is intended to overcome the problems associated with lead fracture and electrode dislodgement. A system and method are disclosed for introducing the unitary pacemaker through a transvenous route, lodging it deeply in the right ventricular apex, and deploying the active fixation barbs. Other implantation sites are suggested, including in relation to sphincters, but no particular examples of the implantation are described. The disclosed unitary pacemaker has not been clinically implanted in humans.

To our knowledge, none of the above-described medical devices have been employed in the field of gastrointestinal stimulation. There remains a need to provide an implantable GI tract stimulator for providing GI tract electrical stimulation at sites in the stomach that can be introduced into the stomach cavity and affixed to the stomach wall without an invasive surgical procedure, that is simple to affix at a desired site, that is securely affixed for temporary or chronic stimulation, and that can be removed when necessary.

SUMMARY OF THE INVENTION

The present invention is preferably embodied in a GI tract stimulator or monitor IMD that can be introduced through the esophagus, that is simple to affix to the stomach or GI tract wall at a desired site, that is securely affixed thereto, and that can be removed when necessary. The IMD is preferably a GI tract stimulator and/or a physiologic signal monitor.

The GI tract stimulator or monitor of the present invention comprises a hermetically sealed housing enclosing electrical stimulation and/or monitoring circuitry and a power source and an elongated flexible member extending from the housing to an active fixation mechanism adapted to be fixed into the mucosa or sub-mucosal tissue. After fixation is effected, the elongated flexible member bends into a preformed shape that presses the housing against the mucosa so that forces that would tend to dislodge the fixation mechanism are minimized.

Preferably, a GI tract stimulator or monitor IMD in accordance with the present invention comprises a hermetically sealed housing enclosing electrical stimulation and/or monitoring circuitry and a power source and supporting a first stimulation/sense electrode adapted to press against the mucosa of the stomach wall. An elongated flexible member is fixed at a member fixed end to the housing and extends away from the housing to a member free end supporting an active fixation mechanism and a second stimulation/sense electrode. The active fixation mechanism is adapted to grip a fold of the mucosa or perforate the mucosa and lodge in the muscularis externa of the GI tract wall when introduced against the mucosa. The active fixation mechanism and second stimulation/sense electrode can be separately supported at the member free end or combined together. A conductor is encased within or extends through a first lumen of the flexible member and is coupled to the second stimulation/sense electrode and to the IPG circuitry within the hermetically sealed housing.

The flexible member is formed to assume a bend intermediate the member fixed end and the member free end when the flexible member is unrestrained. However, the flexible member can be straightened to axially align and enable the introduction of the straightened flexible member and hermetically sealed housing through the lumen of an esophageal catheter. Preferably, an elongated beam of shape memory alloy having the bend formed in it is encased within or extends through a second lumen of the flexible member.

In use, the GI tract stimulator or monitor IMD is fitted into the lumen of an esophageal tube or catheter with the fixation mechanism aimed toward the catheter distal end opening whereby the bend in the flexible member is straightened and the fixation mechanism is contained within the catheter lumen. The catheter (and endoscope) is inserted through a curved mouth and throat guard inserted into the patient's mouth, and the catheter distal end is advanced through the esophagus and lower esophageal sphincter and into the stomach cavity. An endoscope can also be inserted through the catheter lumen or alongside the esophageal catheter to enable visualization of the stomach wall to locate a fixation site and to observe the fixation. The catheter distal end is directed to the site of implantation The fixation mechanism is then deployed to fix the flexible member free end to the stomach wall. The fixation mechanism can be any of those employed to fix IMDs in the body. Preferred forms of fixation mechanisms comprise a helix, one or more hook, or clips or pincers that penetrate through the mucosa into the muscularis externa or pinch a fold of the mucosa. The mucosa can be drawn against the esophageal catheter distal end by drawing suction through the catheter lumen. The fixation mechanism is then pushed or screwed into the stomach wall or the clip or pincers are released to engage the stomach wall fold.

Then, the esophageal catheter is withdrawn to release the GI tract stimulator, whereupon the flexible member assumes its bent configuration and lodges the hermetically sealed housing against the mucosa. The first stimulation/sense electrode is preferably an exposed conductive portion of the housing that is aligned with the bend of the flexible member so that it is pressed against the mucosa.

For temporary use, the fixation mechanism can be made of a material that is degraded by stomach acid over time to release the GI tract stimulator or monitor IMD and allow it to pass through the GI tract. Alternatively, the removal can be effected by straightening the bend and withdrawing the GI tract stimulator or monitor IMD through the lumen of an esophageal catheter introduced in the same way into the stomach. A wire can be advanced through the catheter lumen to snare or otherwise engage the GI tract stimulator and draw it into the catheter lumen.

The active fixation mechanisms preferably extend away from a stop or plate of the electrode head and are shaped to penetrate through the mucosa and into the muscularis externa upon application of penetrating force through the electrode head to the GI tract wall to draw the stop or plate against the mucosa and operatively contact the stimulation/sense electrode with the GI tract wall. The stop or plate inhibits further advancement of the active fixation mechanism and perforation of the GI tract wall, and the active fixation mechanism cooperates with the stop or plate to inhibit dislodgement of the stimulation/sense electrode from operative contact with the GI tract wall.

The active fixation mechanisms are selected from helixes and barbed hooks having sharpened tips or free ends that perforate the mucosa and lodge in the muscularis externa or the submucosa. The maximal depth of penetration from the stop or plate is preferably in the range of 1 mm to 15 mm when the site comprises the antrum or in the range of 1 mm to 10 mm when the site comprises corpus or fundus to ensure that the free end does not extend substantially through the stomach wall.

The helixes and hooks can be formed of bio-compatible conductive materials that are coupled with the lead conductors and un-insulated at least in part to operate as the sensing and/or stimulation electrodes. The stimulation/sense electrode surface can be coated with a porous platinized structure to reduce polarization and/or an anti-inflammatory agent that inhibits inflammation that can negatively affect the ability to sense electrical signals of the GI tract or to efficiently deliver electrical stimulation. The anti-inflammatory agents can be embedded into a monolithic controlled release device (MCRD) carried by the electrode head.

The expression "stimulation/sense electrode" as used herein applies to stimulation electrodes that are employed to stimulate tissue or sense electrodes to sense electrical signals in the tissue or electrodes that are used to perform both functions.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. In accordance with an aspect of the present invention, improved GI tract stimulation and sensing leads and methods and systems for effecting sensing and stimulation of at least one organ or region of the GI tract are provided. The GI tract stimulator IPG or monitor IMD are depicted in the figures coupled to the stomach wall through use of the fixation mechanisms of the present invention. However, it will be understood that the GI tract stimulator IPG or monitor IMD may be affixed along or to any of the other structures and organ walls along the GI tract, including the colon, small intestine, stomach, or even the esophagus.

Figure 1:
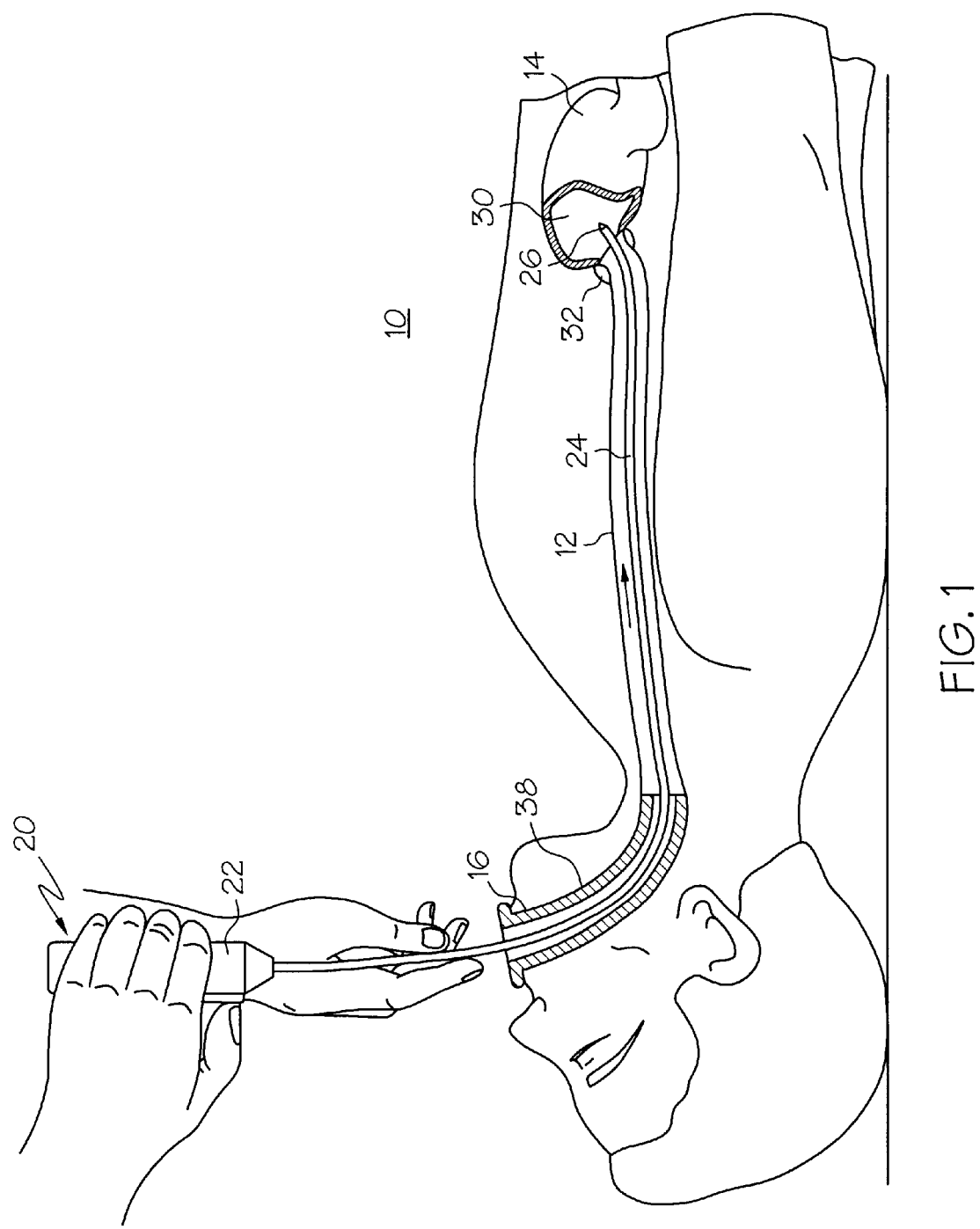
FIG. 1 is a schematic view of obtaining access into the stomach employing an esophageal catheter and optionally employing an endoscope to enable the implantation of a GI tract stimulator IPG or monitor IMD in accordance with the invention.

FIG. 1 is a schematic view of obtaining access into the stomach 14 of a patient 10 employing an esophageal catheter 20 and optionally employing an endoscope to enable the implantation of a GI tract stimulator IPG or monitor IMD in accordance with the invention.

The esophageal catheter comprises a handle 22 coupled to the proximal end of an elongated catheter body 24 extending to a catheter body distal end 26. The esophageal catheter encloses at least one esophageal catheter lumen distal end opening at catheter body distal end 26.

In use, the GI tract stimulator or monitor IMD is fitted into the lumen of the esophageal catheter body with the IMD fixation mechanism aimed toward the catheter distal end 26 whereby the bend in the flexible member is straightened and the fixation mechanism is contained within the catheter lumen. The catheter body 24 is inserted through a curved mouth and throat guard 38 inserted into the patient's mouth 16, and the catheter body distal end 26 is advanced through the esophagus 12 and lower esophageal sphincter 32 and into the stomach cavity 30. An endoscope can also be inserted through the catheter lumen or alongside the esophageal catheter body 24 to enable visualization of the stomach wall 34 to locate a fixation site and to observe the fixation. The catheter distal end 26 is directed to the site of implantation in the stomach wall 34, and the GI tract stimulator or monitor IMD is implanted in one of the ways described further below.

Figure 2:
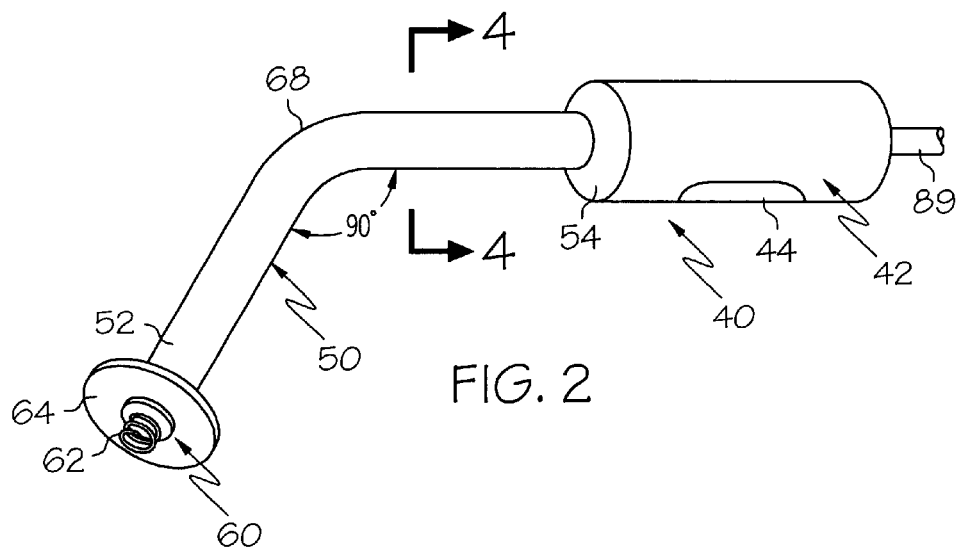
FIG. 2 is a plan view of a GI tract stimulator or monitor IMD comprising a hermetically sealed housing enclosing circuitry and a power source and having a first stimulation/sense electrode adapted to press against the mucosa of the stomach wall coupled through an elongated flexible member extending away from the housing to a member free end supporting an active fixation mechanism and a second stimulation/sense electrode adapted to penetrate the mucosa.

FIG. 2 is a plan view of an exemplary GI tract stimulator or monitor IMD 40 comprising a hermetically sealed housing 42 enclosing circuitry and a power source and having a first stimulation/sense electrode 44 on a surface of the housing 42. The housing 42 is preferably substantially cylindrical having a length greater than its diameter and can have flattened sides. The first stimulation/sense electrode 44 is adapted to press against the mucosa of the stomach wall 34.

An elongated flexible member 50 extends away from the housing 42 to a member free end 52 supporting a combined active fixation mechanism and second stimulation/sense electrode 60 adapted to penetrate the mucosa. The active fixation mechanism is adapted to grip a fold of the mucosa or perforate the mucosa and lodge in the muscularis externa of the GI tract wall when introduced against the mucosa. The active fixation mechanism and second stimulation/sense electrode 60 can be separately supported at the member free end or combined together.

In this example, the active fixation mechanism and second stimulation/sense electrode 60 are combined into a sharpened tip helix 62 mounted to extend from a plate 64 of an electrode head 66 at the flexible member free end 52. The depicted helix 62 comprising one or more coil turn extending from a helix fixed end and a helix free end and having a helix axis, the helix fixed end supported at the plate 64 to extend the helix axis orthogonally to the plate 64. Therefore, the helix 62 is axially aligned with the housing 42 when the GI tract stimulator or monitor IMD 40 is confined within the esophageal lumen 28.

Figure 4:
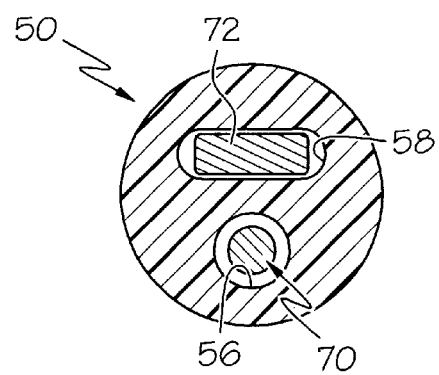
FIG. 4 is a cross-section view taken along lines 4—4 of FIG. 2 showing the shape memory alloy member that imparts the bend in the elongated flexible member when unrestrained and that can be straightened within and advanced through the esophageal catheter lumen.

It will be understood that the second stimulation/sense electrode can be supported on the plate 64 and electrically insulated from the helix 62. The separate electrode can be surface mounted on the plate 64 or can be a projection or pin that is pressed into or through the mucosa. Furthermore, it will be understood that two electrodes can be provided by use of both the helix 62 and such a separate plate mounted electrode The elongated flexible member 50 preferably is formed of a biocompatible, electrical insulating material, e.g. silicone rubber and is fixed at flexible member fixed end 54 to the housing 42. FIG. 4 shows that an electrical conductor 70 is encased within or extends through a first lumen 56 of the flexible member 50 and is coupled to the helix 62 (or other electrode) and to the IPG circuitry within the hermetically sealed housing 42.

Preferably, an elongated leaf spring or beam 72 is encased within the flexible member 50 or extends through a second lumen 58 of the flexible member 50. The elongated beam 72 can be formed of a spring material e.g., a superelastic shape memory alloy, that is pre-shaped to assume a bend 68 of up to substantially 90° intermediate the member fixed end 54 and the member free end 52 when unrestrained as shown in FIG. 2. However, the beam 72 and flexible member 50 can be straightened to axially align and enable the introduction of the straightened flexible member 50 and hermetically sealed housing 42 through the catheter lumen 28 of the esophageal catheter body 24 as shown in FIG. 3.

The preformed and straightenable bend 68 in the elongated flexible member 50 can be formed in many ways. For example, cardiac pacing leads having shaped lead bodies, e.g., J-shaped pacing leads adapted to be lodged in the right atrium, employ a variety of ways of assuming a preformed shape or bend when unrestrained. The lead conductors, e.g. conductor 70 in the illustrated example, can be formed or reinforced to impart such shapes to the lead body that it traverses. Alternatively, shaped beams or additional coils or tubular members are employed in shaping such lead bodies can be substituted for beam 72 in the practice of the present invention.

Figure 3:
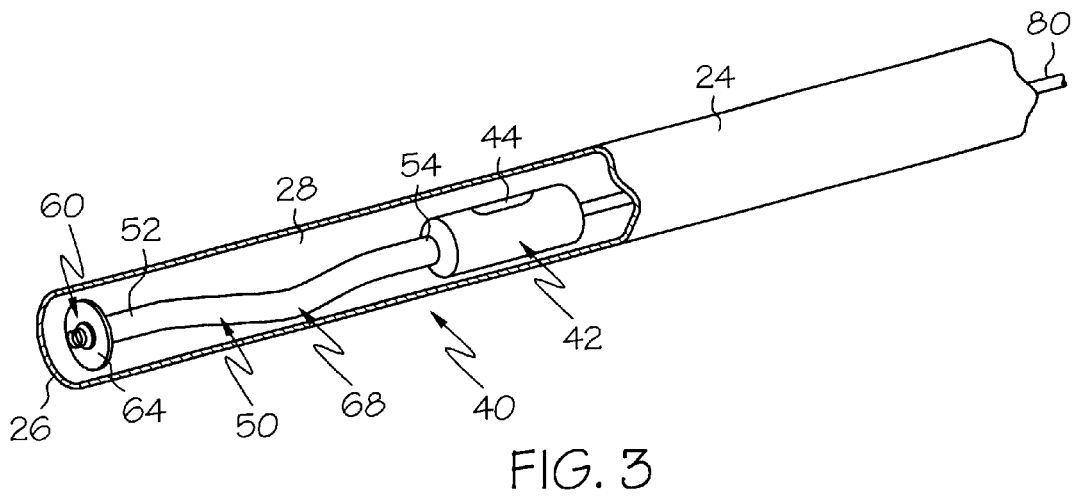
FIG. 3 is a partial view illustrating the confinement of the GI tract stimulator or monitor IMD within the lumen of the esophageal catheter of FIG. 1 thereby substantially straightening the bend in the elongated flexible member of FIG. 2.

In use, the GI tract stimulator or monitor IMD 40 is fitted into the esophageal catheter lumen 28 with the fixation mechanism 60 aimed toward the catheter distal end opening whereby the bend 68 in the flexible member 50 is straightened and the fixation mechanism 60 is contained within the catheter lumen 28 as shown in FIG. 3. An elongated push member 80 can be pushed against or temporarily attached to the proximal end of the housing 42 to push the GI tract stimulator or monitor IMD 40 through the catheter lumen 28. For example, the push member 80 can have a threaded end that is loosely attached to a threaded female connector at the proximal end of the housing 42. In one variation described further below, the push member 80 can comprise a vacuum tube that is coupled with a vacuum port and vacuum lumen of the GI tract stimulator or monitor IMD 40 for providing suction at the active fixation mechanism and second stimulation/sense electrode 60 to draw the mucosa of the stomach wall against active fixation mechanism and second stimulation/sense electrode 60 to help effect fixation.

Figure 5:
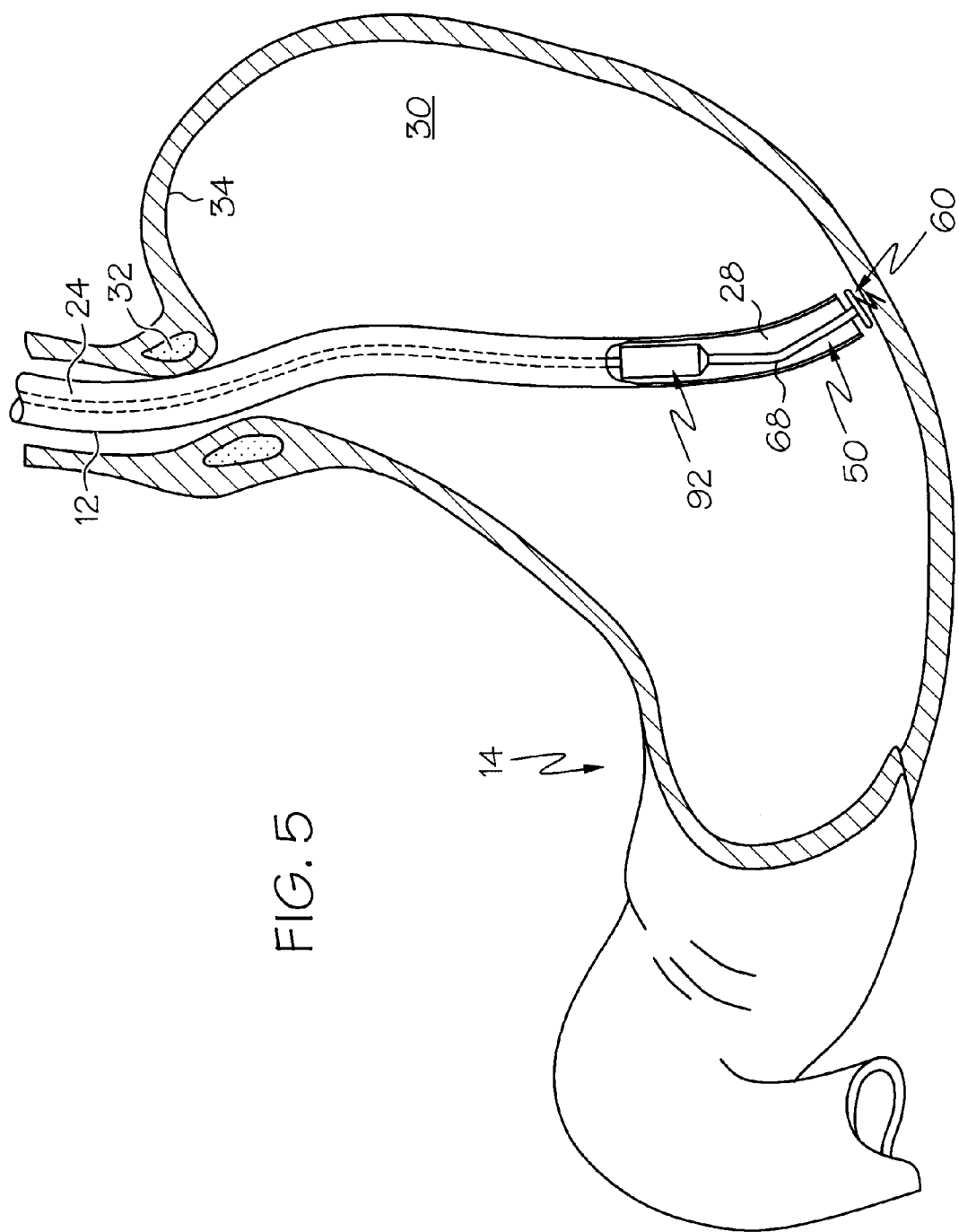
FIG. 5 is a partial view of a distal portion of the esophageal catheter of FIG. 2 located within the stomach cavity and enclosing the GI tract stimulator or monitor IMD within the esophageal catheter lumen as the active fixation mechanism is affixed to the mucosa or sub-mucosa tissue layers.

Then, the esophageal catheter body 24 is inserted through the curved mouth and throat guard 38 inserted into the patient's mouth, and the catheter distal end is advanced through the esophagus and lower esophageal sphincter and into the stomach cavity as shown in FIGS. 1 and 5. An endoscope can also be inserted through the catheter lumen 28 or alongside the esophageal catheter body 24 to enable visualization of the stomach wall 34 to locate a fixation site and to observe the fixation. The catheter distal end 28 is directed to the site of implantation as shown in FIG. 5.

Figure 7:
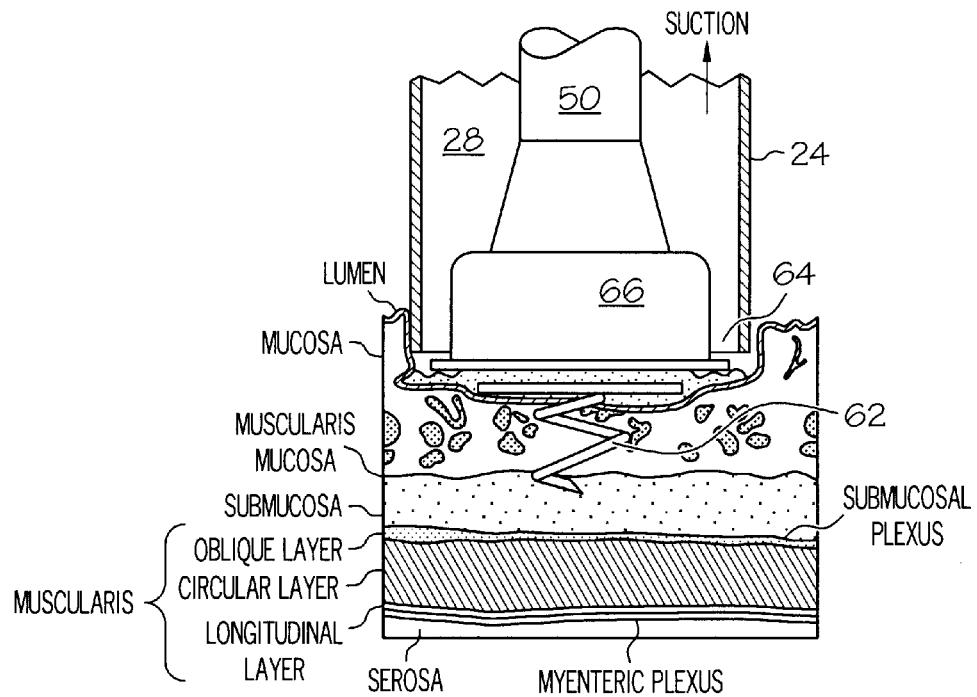
FIG. 7 is an expanded view of an electrode head comprising a screw-in fixation mechanism at the flexible member free end affixed to the mucosa or sub-mucosa tissue layers.

The active fixation and second stimulation/sense electrode 60 is then operated to make the attachment of the elongated member free end 52 to the stomach wall 34 in any of the manners described herein. In particular reference to the helix 62, it is screwed into the mucosa and sub-mucosal tissue by rotating the esophageal catheter 24 or by rotating the push member 80 as shown in FIGS. 5 and 7. In this case, the catheter distal end 26 is pressed into the mucosa and vacuum can be drawn through the catheter lumen 28 to suction the mucosa into the catheter lumen 28 as the helix is screwed through the mucosa, The plate 64 is drawn against the mucosa and operatively contacts any stimulation/sense electrode located on the plate with the mucosa. The plate 64 inhibits further advancement of the active fixation mechanism and perforation of the stomach wall, and the helix 62 cooperates with the plate 64 to inhibit dislodgement of the stimulation/sense electrode (helix 62 in this case) from operative contact with the stomach wall.

In an alternative approach, the helix 62 can be made rotatable by modifying the structure of the housing 42 and the flexible member 50 to allow passage of a further tool, e.g., a shaped tip stylet that can be manipulated from outside the body to rotate the helix 62. In this case, the electrode head 66 comprises a rotatable mechanism fitted into the electrode head 66 and attached to the helix fixed end to extend the helix axis orthogonally to the plate 64, the rotatable mechanism adapted to be engaged by a stylet advanced through the stylet lumen, whereby the rotatable mechanism is rotated by the stylet to rotate the helix and advance the helix free end through the mucosa and into the muscularis externa until the plate is drawn against the mucosa.

Figure 6:
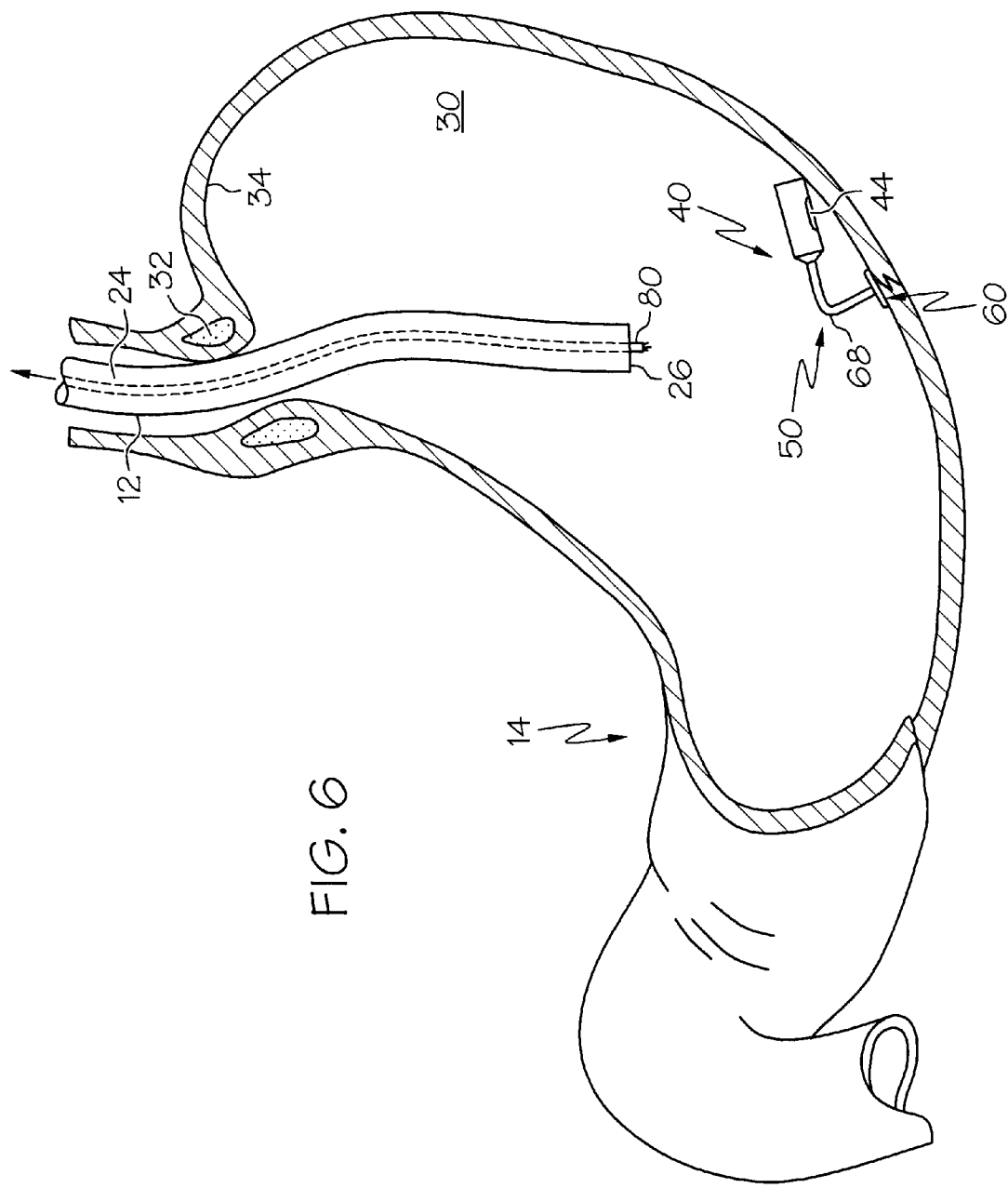
FIG. 6 is a view of the GI tract stimulator or monitor IMD released from the esophageal catheter lumen so that the bend is reformed in the elongated flexible member to press the hermetically sealed housing against the mucosa.

When fixation is effected, the physician retracts the esophageal catheter 20 while holding the push member 80 steady to eject the GI tract stimulator or monitor IMD 40 as shown in FIG. 6. The flexible member 50 assumes its bent configuration and lodges the hermetically sealed housing 42 against the mucosa of the stomach wall 34 as shown in FIG. 6. The first stimulation/sense electrode 44 is preferably an exposed conductive portion of the housing 42 that is aligned with the bend 68 of the flexible member 50 so that the electrode 44 is pressed against the mucosa. The bend 68 diminishes the pendulum-type load on the fixation mechanism 60 that would otherwise be present if the fixation mechanism 60 and the housing 42 remained in axial alignment as shown in the above-referenced '864 patent.

As noted above, the fixation mechanism and second stimulation/sense electrode 60 can take other forms. In FIG.

8, two (or more) barbed hooks 90, 92 project from the plate 64, and the barbed hooks 90, 92 engage sub-mucosal tissue to hold the plate 64 against the mucosa. The barbed fixation hooks 90, 92 can either be a fixation mechanism alone or electrically connected together in unipolar GI tract stimulation embodiments of the invention or can each be coupled to an electrical conductor of flexible member 50 extending to the circuitry within housing 42 in either unipolar or bipolar embodiments of the invention. In this embodiment, suction is preferably provided in the plate 64 by way of a suction lumen of the flexible member 50 and a suction tube extending through or alongside housing 42 to the connection with the push member 80. Suction can be confined within a recess of the plate 64. For example, a pair of suction lumens 80 and 82 are depicted in the cross-section view of FIG. 11.

Figure 8:
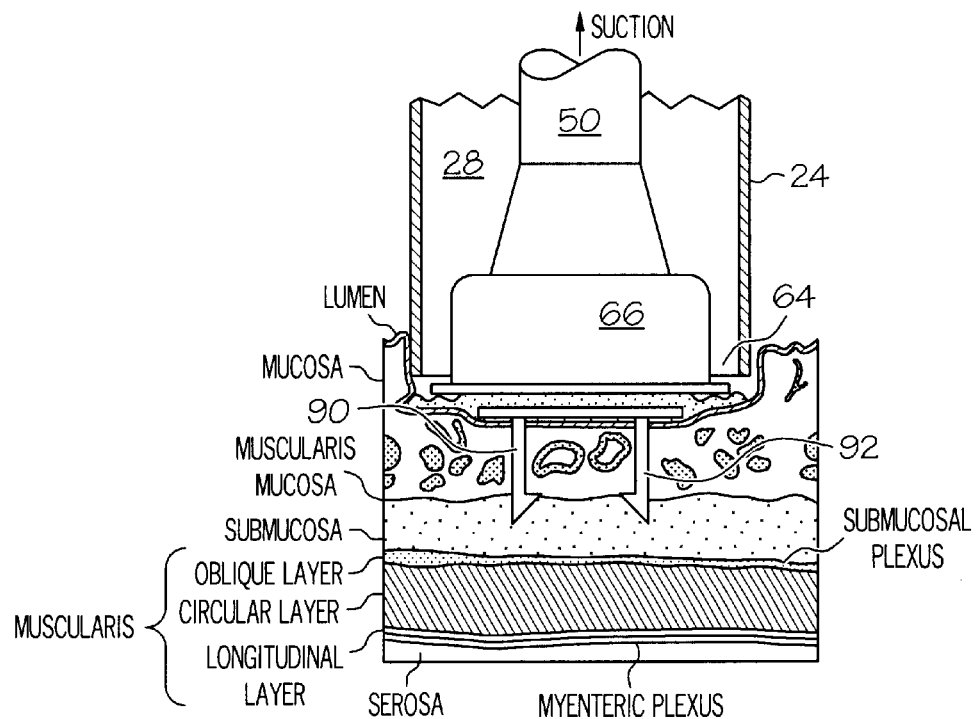
FIG. 8 is an expanded view of an electrode head comprising a hook fixation mechanism at the flexible member free end affixed to the mucosa or sub-mucosa tissue layers.

The stomach wall 34 of the stomach 14 comprises essentially seven layers of tissue that are shown in cross-section in FIGS. 7 and 8. The seven tissue layers include the oblique, circular, and longitudinal muscle layers of the muscularis externa that contract and expand as described above, interposed between the interior stomach mucosa and the external serosa. In the preferred embodiments, the fixation mechanism perforates the mucosa and lodges in the sub-mucosal tissues, e.g., the thickest circular layer muscularis externa. The active fixation mechanisms are selected from helixes and barbed hooks or pincers or the like having sharpened tips or free ends that perforate the mucosa and lodge in the muscularis externa or the submucosa. The maximal depth of penetration of any part of the fixation mechanism from the stop or plate is preferably in the range of 1 mm to 15 mm when the site comprises the antrum or in the range of 1 mm to 10 mm when the site comprises corpus or fundus to ensure that the free end does not extend substantially through the stomach wall.

The fixation hooks or helixes functioning as stimulation/sense electrodes can be formed of bio-compatible conductive materials that are exposed entirely or selectively insulated in portions thereof embedded in the muscularis externa. Other plate-mounted electrodes can also be formed of bio-compatible conductive materials. In all cases, the stimulation/sense electrode surface can be coated with a porous platinized structure to reduce polarization and/or an anti-inflammatory agent that inhibits inflammation that can negatively affect the ability to sense electrical signals of the GI tract or to efficiently deliver electrical stimulation. The anti-inflammatory agents can be embedded into an MCRD carried by the electrode head 66, particularly in the surface of the plate 64. Such anti-inflammatory agents include steroids, anti-bacterial agents, baclofen, dexamethasone sodium phosphate and beclomethasone phosphate.

The electrode head plate 64 can comprise a fabric mesh disc of DACRON or other biocompatible material or a silicone rubber disc or a combination of both that is flexible, biocompatible, and encourages tissue growth adhesion with the mucosa of the GI tract wall. The plate 64 can be substantially planar when unrestrained as depicted in the figures or may have any other convenient curvilinear shape that operates as a stop.

Figure 9:
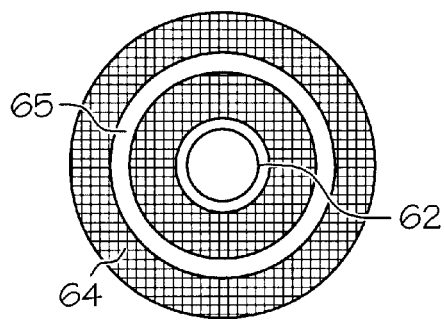
FIG. 9 is an end view of the electrode head of FIG. 7 depicting an example of a stimulation sense electrode separated from the fixation mechanism.

For temporary use, the fixation mechanism can be made of a material that is degraded by stomach acid over time, e.g., polylactic acid compounds, to release the GI tract stimulator or monitor IMD and allow it to pass through the GI tract. Thus, the hooks 90, 92 or screw 62 or pincers or the like could be made of such materials. In this case, a separate stimulation/sense electrode would be mounted on the plate 64. FIG. 9 shows an example of a stimulation sense electrode 65 on the plate 64 separated physically and electrically from the fixation mechanism, which in this illustration comprises helix 62.

Alternatively, the removal of the can be effected by straightening the bend and withdrawing the GI tract stimulator or monitor IMD through the lumen of an esophageal catheter introduced in the same way into the stomach. A wire can be advanced through the catheter lumen to snare or otherwise engage the GI tract stimulator or monitor IMD draw it into the catheter lumen for removal.

One or more sensor can also be built into the GI tract stimulator or monitor IMD 40 for sensing physiologic parameters including pH and pressure so that fluctuations in acidity and pressure waves associated with normal gastric function or distressed gastric function, including gastric reflex symptoms, regurgitation symptoms, bloating or other conditions known in the art, can be recorded and stored in IMD memory.

The IMD circuitry within the IMD 40 preferably comprises a microcomputer based operating system combined with stimulation pulse generating circuitry and/or monitoring circuitry, memory for storing operating instructions and accumulated device operating and patient data, and various other circuits and components well known in the art such as that employed in the Medtronic® Itrel III® Model 7425 IPG.

The GI tract stimulator or monitor IMD 40 includes a telemetry transceiver and antenna (which can be embedded in the elongated flexible member 50 or which can constitute the member 72 or conductor 70) for communication with external medical devices or programmers in a manner well known in the art. Telemetry transmission sessions are initiated between the external medical device and the GI tract stimulator or monitor IMD 40 involving uplink telemetry of stored or real time data and downlink telemetry of commands to modify the operating mode or operating parameters of the GI tract stimulator or monitor IMD 40.

The power source for the IPG and/or monitoring circuitry and operating system can be a miniaturized IMD battery of any of the types known in the art. Alternatively, energy can be transmitted from an external power supply through the skin to an antenna and accumulated by circuitry within the housing 42 providing the power source.

Figure 10:
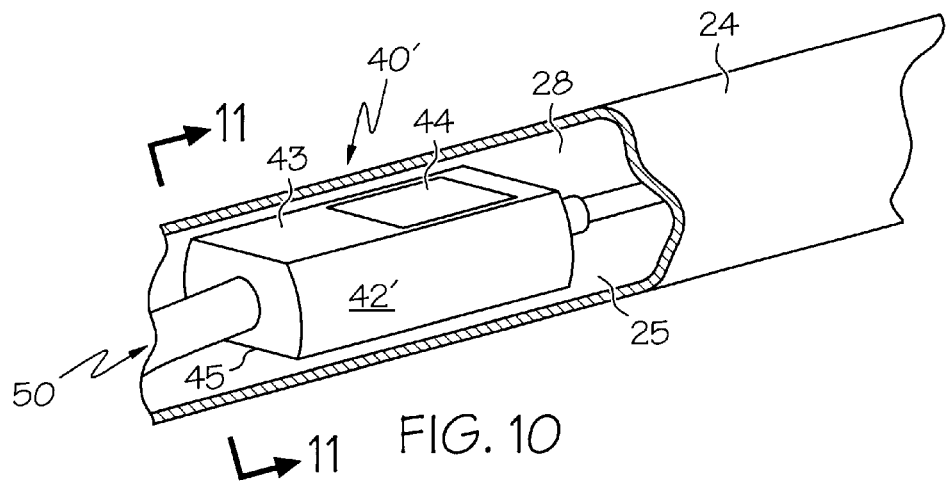
FIG. 10 is a partial view illustrating the confinement of a modified GI tract stimulator or monitor IMD within a modified lumen of the esophageal catheter of FIG. 1 thereby substantially straightening the bend in the elongated flexible member and enhancing ability to rotate the GI tract stimulator or monitor IMD and fixation helix by rotation of the esophageal catheter.
Figure 11:
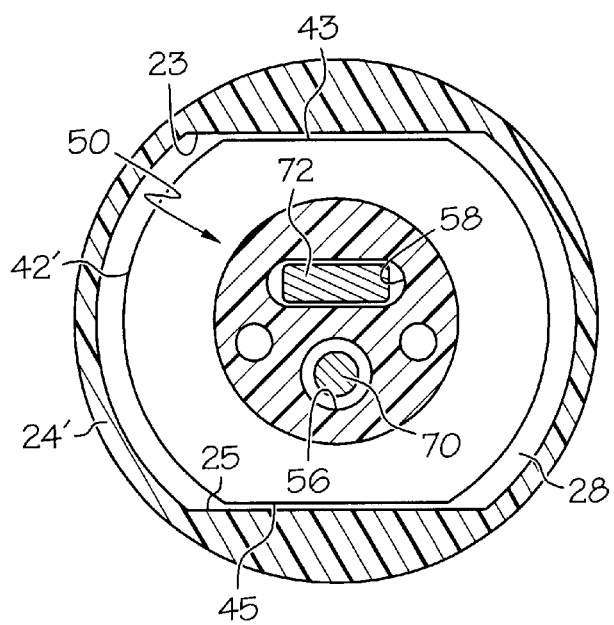
FIG. 11 is a cross-section view taken along the lines 11—11 in FIG. 10 illustrating one example of the shaping of the GI tract stimulator or monitor IMD and the esophageal catheter body to enable engagement therebetween to rotate the GI tract stimulator or monitor IMD and fixation helix by rotation of the esophageal catheter.

As described above, the helix 62 can be rotated in a variety of ways to screw it into the GI tract wall. One preferred way is to rotate the entire assembly of the esophageal catheter 20, the GI tract stimulator or monitor IMD 40, and the push member 80 (if attached to the housing 42) when the helix 62 is positioned at the site as shown in FIG. 5. FIGS. 10 and 11 illustrate one way of imparting rotational torque through the catheter body 24 and minimizing rotation or slippage of the GI tract stimulator or monitor IMD 40 within the catheter lumen 28. In this embodiment, a modified GI tract stimulator or monitor IMD 40' and catheter body 24' provide keyed or locked engagement of flat housing surfaces 43 and 45 of the modified housing 42' with catheter body lumen wall flat surfaces 23 and 25 formed in at least the distal portion of the catheter body 24. The closely spaced flat surfaces prevent the rotation of the GI tract stimulator or monitor IMD 40 within the catheter lumen 28 when the catheter body 24 is rotated. It will be understood that a single flat housing surface 43 and lumen wall flat surface 23 may be sufficient to provide the desired effect or that three or more flat mating surfaces can be formed on the housing 42' and the lumen wall, e.g., mating hexagonal surfaces. Other key mechanisms can also be employed in the distal portion of the catheter body 24 to interact with the housing 42/

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of GI tract neurostimulators are not disclosed and are not necessary to the practice of the present invention. In addition, it will be understood that specifically described structures, functions and operations set forth in the above-referenced patents can be practiced in conjunction with the present invention, but they are not essential to its practice.

Thus, embodiments of the IMPLANTABLE MEDICAL DEVICE AFFIXED WITHIN THE GASTROINTESTINAL TRACT are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A gastrointestinal implantable medical device adapted to be implanted within the GI tract and affixed to the mucosa or sub-mucosal layers of the GI tract wall comprising:
   a hermetically sealed housing enclosing circuitry and a power source;
   an elongated flexible member fixed at a member fixed end to the housing and extending away from the housing to a member free end supporting an active fixation mechanism for attachment to the mucosa or sub-mucosal layers of the GI tract wall; and
   bending means incorporated with the elongated flexible member for bending the elongated member when unrestrained to press the housing against the mucosa so that forces that would tend to dislodge the fixation mechanism are minimized.

2. The implantable medical device of claim 1, wherein the fixation mechanism is formed of a material that dissolves in body fluids over a period of time to release the implantable medical device.

3. The implantable medical device of claim 1, wherein the free end of the elongated flexible member comprises an electrode head supporting the active fixation mechanism and supporting a stimulation/sense electrode and an electrical conductor extending from the stimulation/sense electrode to the circuitry within the hermetically sealed housing.

4. The implantable medical device of claim 3, wherein the electrode head comprises a plate, and the active fixation mechanism comprises a helix affixed to extend from the plate and adapted to be screwed into the mucosa or sub-mucosa layers.

5. The implantable medical device of claim 3, wherein the electrode head comprises a plate, and the active fixation mechanism comprises a hook affixed to extend from the plate and adapted to be pushed into the mucosa or sub-mucosa layers.

6. The implantable medical device of claim 3, further comprising a housing stimulation/sense electrode formed on the housing in alignment with the bending means such that the bending of the bending means presses the housing stimulation/sense electrode against the mucosa.

7. The implantable medical device of claim 1, wherein the free end of the elongated flexible member comprises an electrode head supporting a combined active fixation mechanism and stimulation/sense electrode and an electrical conductor extending from the stimulation/sense electrode to the circuitry within the hermetically sealed housing.

8. The implantable medical device of claim 7, wherein the electrode head comprises a plate, and the active fixation mechanism comprises a helix affixed to extend from the plate and adapted to be screwed into the mucosa or sub-mucosa layers.

9. The implantable medical device of claim 7, wherein the electrode head comprises a plate, and the active fixation mechanism comprises a hook affixed to extend from the plate and adapted to be pushed into the mucosa or sub-mucosa layers.

10. The implantable medical device of claim 7, further comprising a housing stimulation/sense electrode formed on the housing in alignment with the bending means such that the bending of the bending means presses the housing stimulation/sense electrode against the mucosa.

11. The implantable medical device of claim 1, wherein the electrode head comprises a plate, the attachment mechanism extends from the plate to engage the GI tract wall and inhibit dislodgement of the stimulation/sense electrode from operative contact with the GI tract wall, and the plate inhibits further advancement of the active fixation mechanism and perforation of the GI tract wall.

12. The implantable medical device of claim 1, wherein:
   the free end of the elongated flexible member comprises an electrode head supporting the active fixation mechanism and supporting a stimulation/sense electrode and an electrical conductor extending from the stimulation/sense electrode to the circuitry within the hermetically sealed housing; and
   the circuitry comprises an electrical stimulation generator that supplies electrical stimulation of the GI tract wall through the stimulation/sense electrode.

13. The implantable medical device of claim 12, wherein the circuitry comprises sensing means for sensing electrical signals of the GI tract through the stimulation/sense electrode.

14. The implantable medical device of claim 1, wherein:
   the free end of the elongated flexible member comprises an electrode head supporting the active fixation mechanism and supporting a stimulation/sense electrode and an electrical conductor extending from the stimulation/sense electrode to the circuitry within the hermetically sealed housing; and
   the circuitry comprises sensing means for sensing electrical signals of the GI tract through the stimulation/sense electrode.

15. The implantable medical device of claim 1, wherein:
   the housing supports a first stimulation/sense electrode coupled with the circuitry in the housing in alignment with the bending means such that the bending of the bending means presses the housing stimulation/sense electrode against the mucosa.
   the free end of the elongated flexible member comprises an electrode head supporting the active fixation mechanism and supporting a second stimulation/sense electrode and an electrical conductor extending from the stimulation/sense electrode to the circuitry within the hermetically sealed housing; and
   the circuitry comprises an electrical stimulation generator that supplies electrical stimulation of the GI tract wall through the first and second stimulation/sense electrodes.

16. The implantable medical device of claim 1, wherein:
   the housing supports a first stimulation/sense electrode coupled with the circuitry in the housing in alignment with the bending means such that the bending of the bending means presses the housing stimulation/sense electrode against the mucosa.

the free end of the elongated flexible member comprises an electrode head supporting the active fixation mechanism and supporting a second stimulation/sense electrode and an electrical conductor extending from the stimulation/sense electrode to the circuitry within the hermetically sealed housing; and the circuitry comprises an electrical signal monitor that detects electrical signals of the GI tract wall through the first and second stimulation/sense electrodes.

17. The implantable medical device of claim 1, further comprising a housing stimulation/sense electrode formed on the housing in alignment with the bending means such that the bending of the bending means presses the housing stimulation/sense electrode against the mucosa.

18. The implantable medical device of claim 1, wherein an anti-inflammatory material selected from the group consisting of steroids, anti-bacterial agents, baclofen, dexamethasone sodium phosphate or beclomethasone phosphate is incorporated into the electrode head or fixation mechanism.

19. The implantable medical device of claim 1, wherein:
the member free end comprises a plate; and
the active fixation mechanism comprises a helix comprising one or more coil turn extending from a helix fixed end and a helix free end and having a helix axis, the helix fixed end supported at the plate to extend the helix axis orthogonally to the plate, the helix free end adapted to penetrate through the mucosa and the helix adapted to advance into the muscularis externa upon rotation of the helix until the plate is drawn against the mucosa.

20. The implantable medical device of claim 19, wherein the helix has an axial length enabling a depth of penetration from the plate in the range of 1 mm to 15 mm when the site comprises the antrum of the stomach wall or in the range of 1 mm to 10 mm when the site comprises corpus or fundus of the stomach wall to ensure that the helix free end does not extend substantially through the stomach wall.

21. The implantable medical device of claim 19, wherein a stimulation/sense electrode is supported on the plate of the electrode head to press against the mucosa when the plate is drawn against the mucosa.

22. The implantable medical device of claim 1, wherein:
the member free end comprises a plate; and
the active fixation mechanism comprises a hook comprising a hook shaft extending from a hook fixed end attached to an electrode head to a hook free end spaced from the plate, a sharpened tip formed at the hook free adapted to penetrate through the mucosa and to advance into the muscularis externa when insertion force is applied to the electrode head until the plate is drawn against the mucosa, whereupon advancement of the hook free end is halted.

23. The implantable medical device of claim 22, wherein the hook has an axial length enabling a depth of penetration from the plate in the range of 1 mm to 15 mm when the site comprises the antrum of the stomach wall or in the range of 1 mm to 10 mm when the site comprises corpus or fundus of the stomach wall to ensure that the hook free end does not extend substantially through the stomach wall.

24. The implantable medical device of claim 22, wherein a stimulation/sense electrode is supported on the plate of the electrode head to press against the mucosa when the plate is drawn against the mucosa.

25. The implantable medical device of claim 1, further comprising a physiologic sensor for sensing a physiologic state of the GI tract.

26. A method of implanting a gastrointestinal implantable medical device (IMD) within the gastrointestinal tract (GI tract) comprising:

forming the IMD with a hermetically sealed housing having a housing axis enclosing circuitry and a power source and with an elongated flexible member fixed at a member fixed end to the housing and extending away from the housing to a member free end supporting an active fixation mechanism, the elongated flexible member incorporating a bendable beam that imparts a bend in the elongated member to bend the active fixation mechanism out of axial alignment with the housing when unrestrained;

inserting the IMD into the lumen of an esophageal catheter body thereby restraining the flexible member and substantially reducing the bend;

advancing the esophageal catheter body through the esophagus to locate the active fixation mechanism at an attachment site of the GI tract wall within the GI tract;

fixing the active fixation mechanism to the GI tract wall at the attachment site; and ejecting the IMD from the esophageal catheter lumen to enable the formation of the bend in the elongated flexible member to press the housing against the GI tract wall so that forces that would tend to dislodge the fixation mechanism are minimized.

27. The method of claim 26, wherein the active fixation mechanism comprises a helix adapted to be screwed into the mucosa or sub-mucosal layers of the GI tract, and the esophageal catheter body and the housing are shaped to mutually engage and inhibit rotation of the housing within the catheter body lumen, and wherein:

the fixing step comprises rotating the catheter body and the IMD to screw the helix into the mucosa or sub-mucosal layers of the GI tract 28. A system for implanting a gastrointestinal implantable medical device (IMD) within the gastrointestinal tract (GI tract) comprising:

an IMD formed with a hermetically sealed housing having a housing axis enclosing circuitry and a power source and with an elongated flexible member fixed at a member fixed end to the housing and extending away from the housing to a member free end supporting an active fixation mechanism, the elongated flexible member incorporating a bendable beam that imparts a bend in the elongated member to bend the active fixation mechanism out of axial alignment with the housing when unrestrained;

an esophageal catheter having an esophageal catheter body and catheter lumen into which the IMD is insertable whereupon the flexible member is restrained and the bend in the flexible member is substantially reduced, the esophageal catheter body adapted to be advanced through the esophagus to locate the active fixation mechanism at an attachment site of the GI tract wall within the GI tract;

means for fixing the active fixation mechanism to the GI tract wall at the attachment site; and means for ejecting the IMD from the esophageal catheter lumen to enable the formation of the bend in the elongated flexible member to press the housing against the GI tract wall so that forces that would tend to dislodge the fixation mechanism are minimized.

29. The system of claim 28, wherein the esophageal catheter body and the housing are shaped to mutually engage and inhibit rotation of the housing within the catheter body lumen.

30. The system of claim 28, wherein the active fixation mechanism comprises a helix adapted to be screwed into the mucosa or sub-mucosal layers of the GI tract, and the esophageal catheter body and the housing are shaped to mutually engage and inhibit rotation of the housing within the catheter body lumen, whereby the catheter body and the IMD are rotatable to screw the helix into the mucosa or sub-mucosal layers of the GI tract.

* * * * *